United States Patent
Swift et al.

(10) Patent No.: US 8,551,344 B2
(45) Date of Patent: Oct. 8, 2013

(54) METHOD AND APPARATUS FOR PRODUCING AUTOLOGOUS CLOTTING COMPONENTS

(75) Inventors: Matthew Swift, Fort Wayne, IN (US); Barry F. Hecker, Pierceton, IN (US); Michael D. Leach, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 355 days.

(21) Appl. No.: 12/757,492

(22) Filed: Apr. 9, 2010

(65) Prior Publication Data

US 2010/0198130 A1 Aug. 5, 2010

Related U.S. Application Data

(62) Division of application No. 11/116,153, filed on Apr. 27, 2005, now Pat. No. 7,694,828.

(51) Int. Cl.
*B01D 37/00* (2006.01)
*B01D 61/00* (2006.01)
*C02F 1/00* (2006.01)

(52) U.S. Cl.
USPC ........... 210/767; 210/738; 210/787; 210/754; 210/749; 604/5.01

(58) Field of Classification Search
None
See application file for complete search history.

(56) References Cited

U.S. PATENT DOCUMENTS

| | | |
|---|---|---|
| 3,723,244 A | 3/1973 | Breillatt, Jr. |
| 3,850,369 A | 11/1974 | Bull et al. |
| 3,897,343 A | 7/1975 | Ayres |
| 3,909,419 A | 9/1975 | Ayres |
| 3,931,010 A | 1/1976 | Ayres et al. |
| 3,931,018 A | 1/1976 | North, Jr. |
| 3,982,691 A | 9/1976 | Schlutz |
| 4,046,699 A | 9/1977 | Zine, Jr. |
| 4,055,501 A | 10/1977 | Cornell |
| 4,077,396 A | 3/1978 | Wardlaw et al. |
| 4,154,690 A | 5/1979 | Ballies et al. |
| 4,187,979 A | 2/1980 | Cullis et al. |
| 4,322,298 A | 3/1982 | Persidsky |
| 4,379,849 A | 4/1983 | Heimreid |
| 4,416,654 A | 11/1983 | Schoendorfer et al. |
| 4,464,167 A | 8/1984 | Schoendorfer et al. |

(Continued)

FOREIGN PATENT DOCUMENTS

| | | |
|---|---|---|
| EP | 0244834 A2 | 11/1987 |
| EP | 1079224 A2 | 2/2001 |

(Continued)

OTHER PUBLICATIONS

European Search Report completed on Aug. 24, 2006 for EP06242170 claiming benefit of U.S. Appl. No. 11/116,153, filed Apr. 27, 2005.

(Continued)

*Primary Examiner* — Dirk Bass
(74) *Attorney, Agent, or Firm* — Harness, Dickey

(57) ABSTRACT

A method and apparatus for obtaining various components of a multi-component material. Generally, a component of a whole blood sample may be concentrated from a patient and re-introduced to the same patient. For example, a clotting component, such as thrombin, from a whole blood sample may be extracted and concentrated in an apparatus and collection to be reapplied or reintroduced into a patient.

30 Claims, 10 Drawing Sheets

(56) References Cited

U.S. PATENT DOCUMENTS

| | | |
|---|---|---|
| 4,675,117 A | 6/1987 | Neumann et al. |
| 4,714,457 A | 12/1987 | Alterbaum |
| 4,776,964 A | 10/1988 | Schoendorfer et al. |
| 4,818,386 A | 4/1989 | Burns |
| 5,019,243 A | 5/1991 | McEwen et al. |
| 5,053,127 A | 10/1991 | Schoendorfer et al. |
| 5,131,907 A | 7/1992 | Williams et al. |
| 5,141,645 A | 8/1992 | Shiraki et al. |
| 5,147,290 A | 9/1992 | Jonsson et al. |
| 5,165,938 A | 11/1992 | Knighton |
| 5,171,456 A | 12/1992 | Hwang et al. |
| 5,185,001 A | 2/1993 | Galanakis |
| 5,234,608 A | 8/1993 | Duff |
| 5,269,927 A | 12/1993 | Fiehler |
| 5,271,852 A | 12/1993 | Luoma, II |
| 5,318,782 A | 6/1994 | Weis-Fogh et al. |
| 5,322,620 A | 6/1994 | Brown et al. |
| 5,344,752 A | 9/1994 | Murphy |
| 5,370,802 A | 12/1994 | Brown |
| 5,376,263 A | 12/1994 | Fischel |
| 5,387,187 A | 2/1995 | Fell et al. |
| 5,403,272 A | 4/1995 | Deniega et al. |
| 5,456,885 A | 10/1995 | Coleman et al. |
| 5,494,578 A | 2/1996 | Brown et al. |
| 5,494,592 A | 2/1996 | Latham, Jr. et al. |
| 5,501,371 A | 3/1996 | Schwartz-Feldman |
| 5,549,683 A | 8/1996 | Bonutti |
| 5,560,830 A | 10/1996 | Coleman et al. |
| 5,585,007 A | 12/1996 | Antanavich et al. |
| 5,601,727 A | 2/1997 | Bormann et al. |
| 5,607,579 A | 3/1997 | Latham, Jr. et al. |
| 5,614,106 A | 3/1997 | Payrat et al. |
| 5,632,895 A | 5/1997 | Tsukagoshi et al. |
| 5,632,905 A | 5/1997 | Haynes |
| 5,649,903 A | 7/1997 | Deniega et al. |
| 5,707,331 A | 1/1998 | Wells et al. |
| 5,707,876 A | 1/1998 | Levine |
| 5,733,466 A | 3/1998 | Benebo et al. |
| 5,733,545 A | 3/1998 | Hood, III |
| 5,788,662 A | 8/1998 | Antanavich et al. |
| 5,795,571 A | 8/1998 | Cederholm-Williams et al. |
| 5,795,751 A | 8/1998 | Apel |
| 5,817,519 A | 10/1998 | Zelmanovic et al. |
| 5,833,866 A | 11/1998 | Brown |
| 5,834,418 A | 11/1998 | Brazeau et al. |
| 5,837,150 A | 11/1998 | Langley et al. |
| 5,863,892 A | 1/1999 | Stern et al. |
| 5,865,785 A | 2/1999 | Bischof |
| 5,899,874 A | 5/1999 | Jonsson et al. |
| 5,900,245 A | 5/1999 | Sawhney et al. |
| 5,934,803 A | 8/1999 | Hutter |
| 5,938,621 A | 8/1999 | Kelly et al. |
| 5,955,032 A | 9/1999 | Kelly et al. |
| 5,955,436 A | 9/1999 | Kunkle, Jr. |
| 5,958,250 A | 9/1999 | Brown et al. |
| 5,958,253 A | 9/1999 | Holm et al. |
| 5,980,734 A | 11/1999 | Itoh et al. |
| 6,010,627 A | 1/2000 | Hood, III |
| 6,022,306 A | 2/2000 | Dumont et al. |
| 6,025,201 A | 2/2000 | Zelmanovic et al. |
| 6,027,655 A | 2/2000 | Holm |
| 6,051,146 A | 4/2000 | Green et al. |
| 6,051,147 A | 4/2000 | Bischof |
| 6,053,856 A | 4/2000 | Hlavinka |
| 6,054,122 A | 4/2000 | MacPhee et al. |
| 6,063,297 A | 5/2000 | Antanavich et al. |
| 6,063,624 A | 5/2000 | Kandler et al. |
| 6,071,421 A | 6/2000 | Brown |
| 6,071,422 A | 6/2000 | Hlavinka et al. |
| 6,071,423 A | 6/2000 | Brown et al. |
| 6,090,793 A | 7/2000 | Zimmermann et al. |
| 6,096,309 A | 8/2000 | Prior et al. |
| 6,117,425 A | 9/2000 | MacPhee et al. |
| 6,196,987 B1 | 3/2001 | Holmes et al. |
| 6,197,325 B1 | 3/2001 | MacPhee et al. |
| 6,200,287 B1 | 3/2001 | Keller et al. |
| 6,214,338 B1 | 4/2001 | Antanavich et al. |
| 6,245,900 B1 | 6/2001 | Yamasaki et al. |
| 6,274,090 B1 | 8/2001 | Coelho et al. |
| 6,280,400 B1 | 8/2001 | Niermann |
| 6,296,602 B1 | 10/2001 | Headley |
| 6,368,298 B1 | 4/2002 | Beretta et al. |
| 6,417,004 B1 | 7/2002 | Brady et al. |
| 6,444,228 B1 | 9/2002 | Baugh et al. |
| 6,472,162 B1 | 10/2002 | Coelho et al. |
| 6,516,953 B1 | 2/2003 | DiCesare et al. |
| 6,596,180 B2 | 7/2003 | Baugh et al. |
| 6,719,901 B2 | 4/2004 | Dolecek et al. |
| 6,733,471 B1 | 5/2004 | Ericson et al. |
| 6,905,612 B2 | 6/2005 | Dorian et al. |
| 7,179,391 B2 | 2/2007 | Leach et al. |
| 7,553,413 B2 | 6/2009 | Dorian et al. |
| 2002/0090711 A1 | 7/2002 | Karlsson |
| 2002/0114775 A1 | 8/2002 | Pathak |
| 2002/0169408 A1 | 11/2002 | Beretta et al. |
| 2002/0172666 A1 | 11/2002 | Sacchi et al. |
| 2003/0198687 A1 | 10/2003 | Bennett et al. |
| 2004/0120942 A1 | 6/2004 | McGinnis et al. |
| 2004/0182795 A1 | 9/2004 | Dorian et al. |
| 2004/0251217 A1* | 12/2004 | Leach et al. ............. 210/787 |
| 2005/0109716 A1 | 5/2005 | Leach et al. |
| 2005/0233460 A1* | 10/2005 | Clague et al. ............. 436/69 |
| 2006/0009855 A1 | 1/2006 | Goble et al. |
| 2006/0243676 A1 | 11/2006 | Swift et al. |
| 2009/0236297 A1 | 9/2009 | Dorian et al. |

FOREIGN PATENT DOCUMENTS

| | | |
|---|---|---|
| WO | WO-9812274 A1 | 3/1998 |
| WO | WO-9967277 A1 | 12/1999 |
| WO | WO-0238610 A1 | 5/2002 |
| WO | WO-02060925 A1 | 8/2002 |
| WO | WO-03099412 A1 | 12/2003 |
| WO | WO-2004009207 A1 | 1/2004 |

OTHER PUBLICATIONS

Fibrostik™ Plasma Concentrator, Attention Operating Surgeon, Cell Factor Technologies, Inc., Jul. 2003.

International Search Report for PCT/US2006/003598 mailed Jan. 6, 2006 claiming benefit of U.S. Appl. No. 60/640,860, filed Feb. 7, 2005.

* cited by examiner

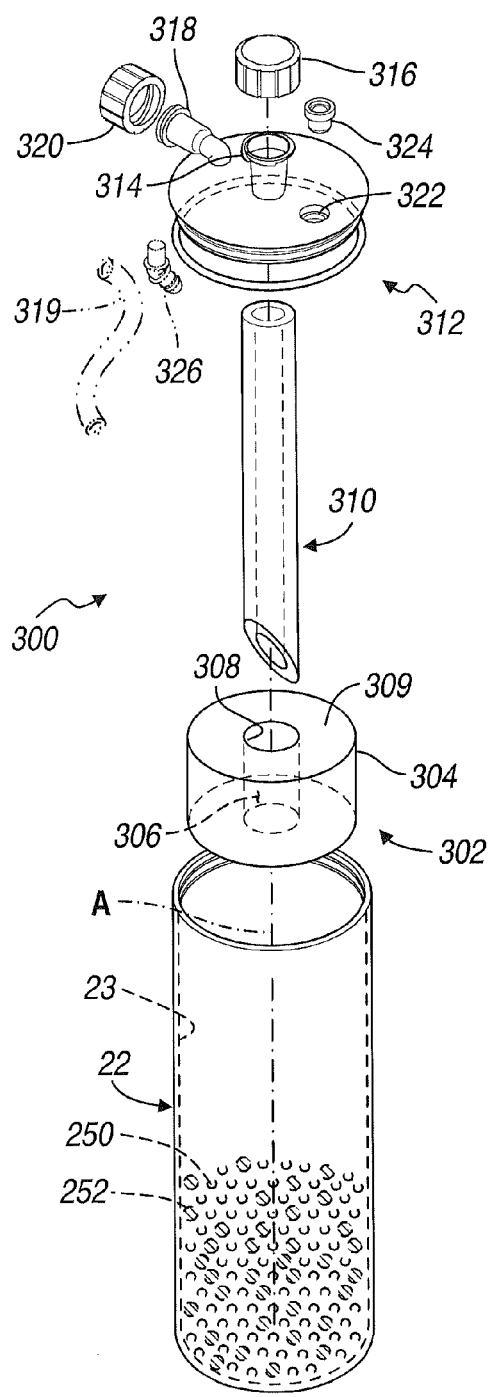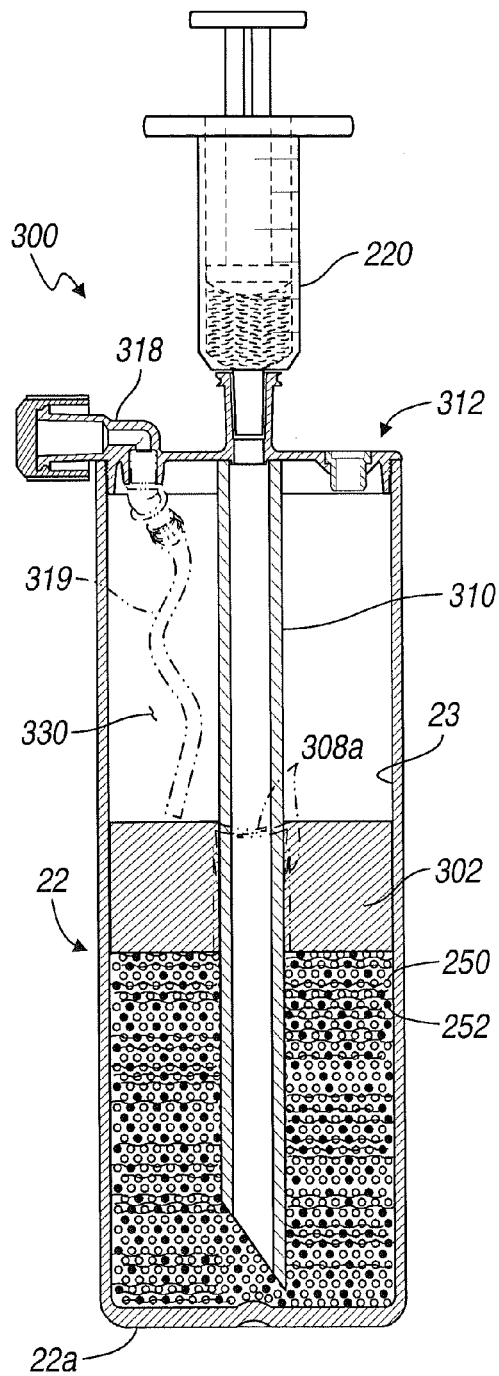
FIG. 4
FIG. 5 ns. The component can include clotting components, such as thrombin, or other components.

According to various embodiments an apparatus for separating components of a multi-component material is taught. The apparatus can include a container operable to contain the multi-component material. An activating bead and a desiccating bead can be positioned in the container and are operable to contact the multi-component material. A mixing assembly can mix the multi-component material and the activating bead and the desiccating bead. The mixing assembly assists in contacting the activating bead with a portion of the multi-component material to activate the portion of the multi-component material and contacting the desiccating bead with the multi-component material can remove a portion of water from the multi-component material.

According to various embodiments a kit for forming a selected component from a whole blood sample is disclosed. The kit can include a first whole blood separation apparatus and a second whole blood separation apparatus. The first whole blood separating apparatus can include a container operable to contain the multi-component material, an activating bead and a desiccating bead positioned in the container and operable to contact the multi-component material, and a mixing assembly operable to mix the multi-component material and the activating bead and the desiccating bead. The second whole blood separation apparatus can includes a container operable to contain a volume of whole blood, a first piston operable to move through the volume of the whole blood, a second piston operable to move through the whole blood and defining a platelet collection area, and a withdrawal member operable to interconnection the platelet collection area and an outlet port. The first whole blood separation device and the second whole blood separation device are can separate and/or concentrate selected and different components of the whole blood sample.

According to various embodiments, a method of separating a clotting component from a whole blood sample in a container having a mixing assembly, desiccating beads, and activating beads is taught. The method can includes collecting a whole blood sample and introducing the whole blood sample into the container. The whole blood sample can be mixed with the desiccating beads and the activating beads with the mixing assembly to activate a portion of the whole blood sample and to withdraw a selected volume of water from the whole blood sample. A volume of a fluid, including concentrated clotting components, can be withdrawn from the container after mixing the whole blood sample with the desiccating beads and the activating beads.

According to various embodiments a device for separating a multi-component material is disclosed. The device can include a container having a first end and a second end operable to contain a multi-component material. A piston can be positioned in the container between the first end and the second end. A delivery tube can be provided that extends from near the first end past the piston and towards the second end operable to position the multi-component material relative to the piston within the container. The container and/or the piston can be selectable between a constraining configuration and a free configuration. When one of the container and/or the piston are in the constraining configuration the piston is held at a selected location in the container and when the container and/or the piston is in the free configuration, the piston is operable to move relative to the container.

BRIEF DESCRIPTION OF THE DRAWINGS

The present teachings will become more fully understood from the detailed description and the accompanying drawings, wherein:

METHOD AND APPARATUS FOR PRODUCING AUTOLOGOUS CLOTTING COMPONENTS

CROSS-REFERENCE TO RELATED APPLICATIONS

Figure 1:
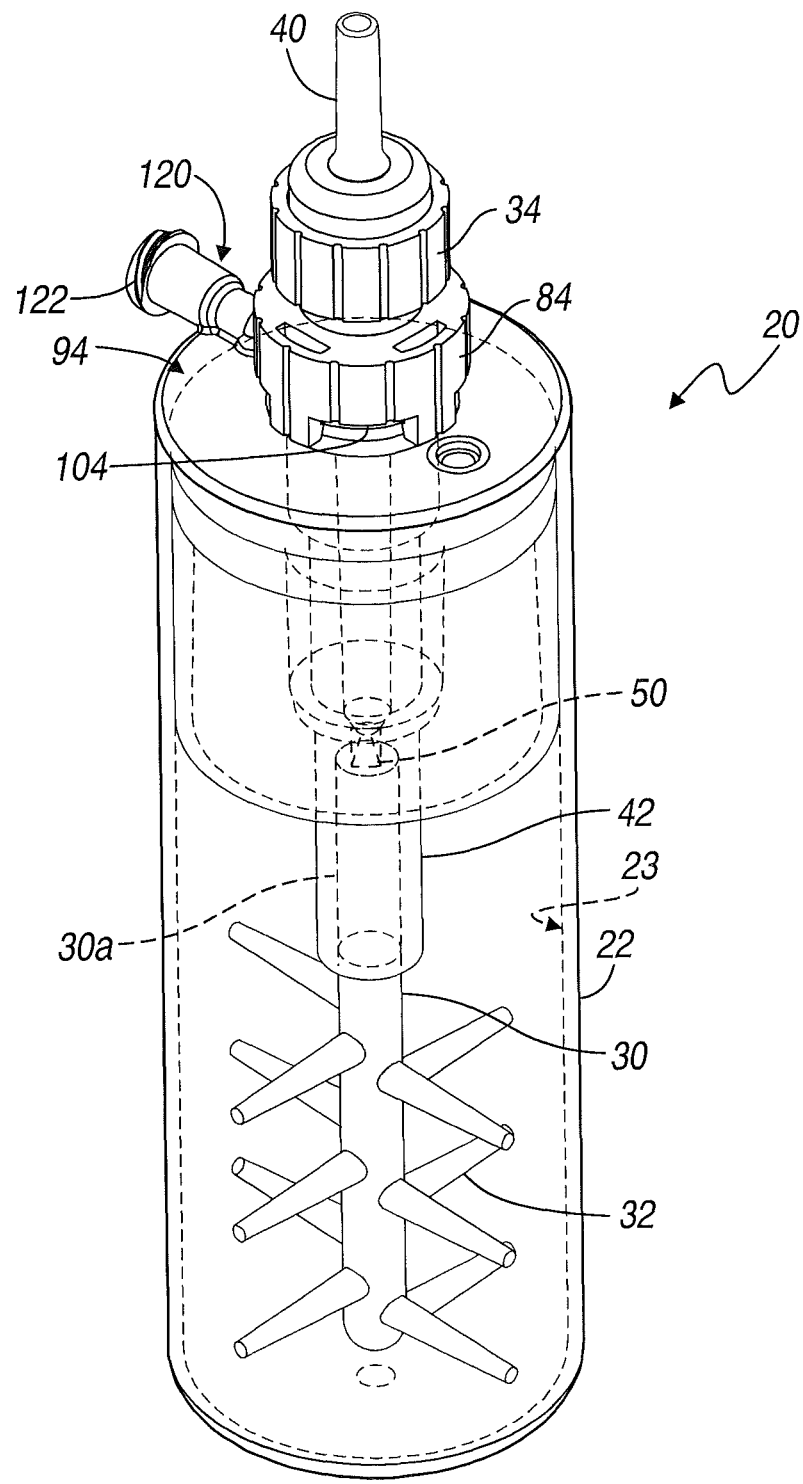

This application is a divisional of U.S. patent application Ser. No. 11/116,153 filed on Apr. 27, 2005. The entire disclosure of the above application is incorporated herein by reference.

FIELD

The present teachings are directed generally to a thrombin collection system, in particular to an autologous thrombin collection and concentration system.

BACKGROUND

In whole blood, such as human whole blood, various proteins, cells, and other components are carried. For example, whole blood includes a plasma fraction which carries a plurality of components such as the red blood cells, erythrocytes, white blood cells or leukocytes, and other components such as platelets. A whole blood sample may include a plurality of clotting factors, such as thrombin. The whole blood sample includes the clotting factors that can form a clot to heal a lesion or other opening.

For various reasons, it may be selected to provide a concentration of the clotting factors, such as thrombin, at a particular location. For example, during a surgical procedure, such as an orthopedic surgical procedure, it may be selected to provide a concentration of the clotting factors relative to the incision site, the implantation site, or the repair site. The clotting factors may assist in healing the incisions in the tissue to reach the injured sites and may assist the body in healing after implantation or augmentation of a selected system.

The clotting components may either be autologous, homologous, or heterologous. For example, it is known to extract bovine thrombin to be used as a clotting factor when performing a procedure on a human. Further, it may be possible to obtain clotting factors from a homologous source, such as a donor human. Nevertheless, it is desirable to have a method and apparatus to use an autologous source to assist in reducing the possibility of rejection or other side effects from using a non-autologous source for providing a clotting factor.

SUMMARY

Figure 2:
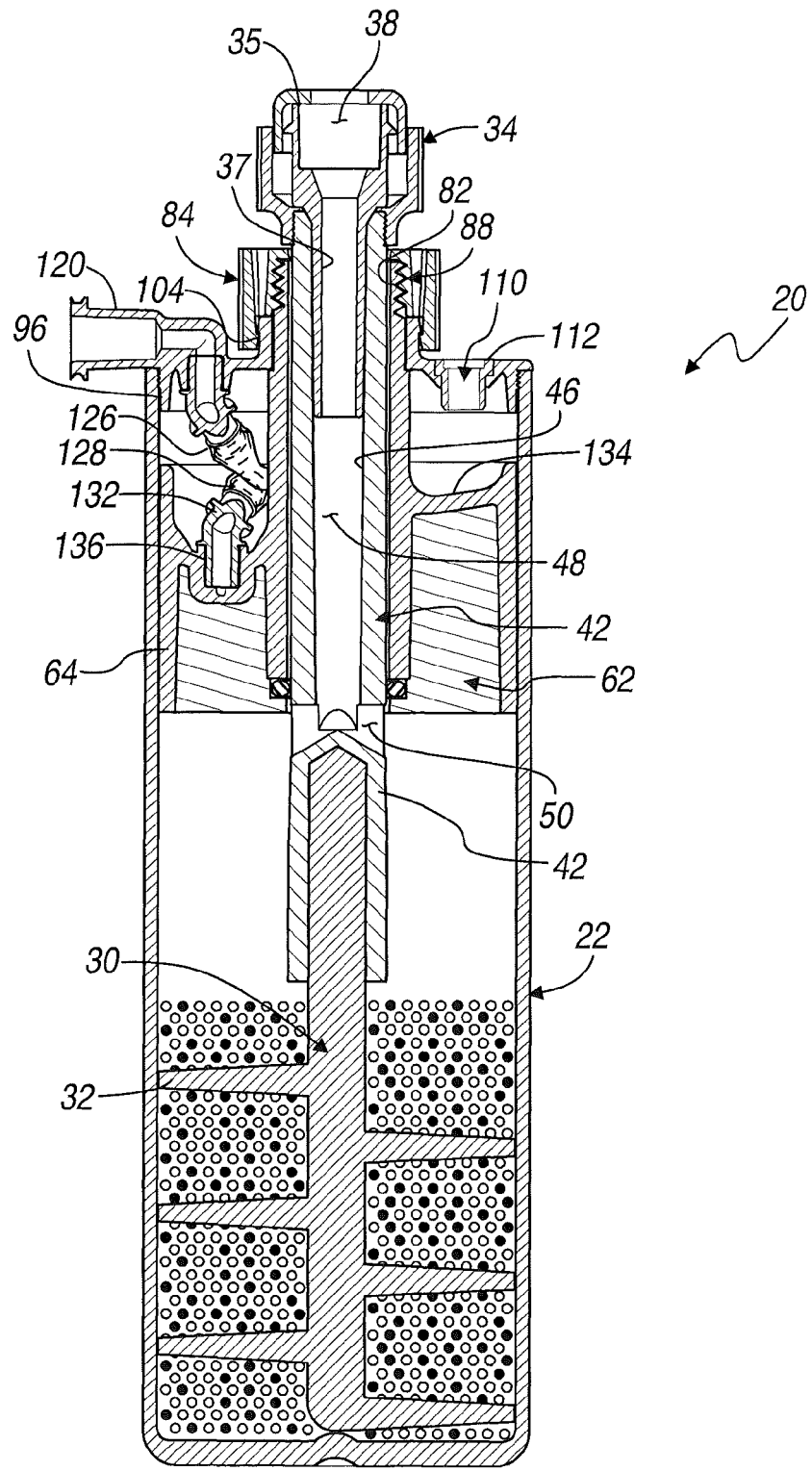
Figure 3A:
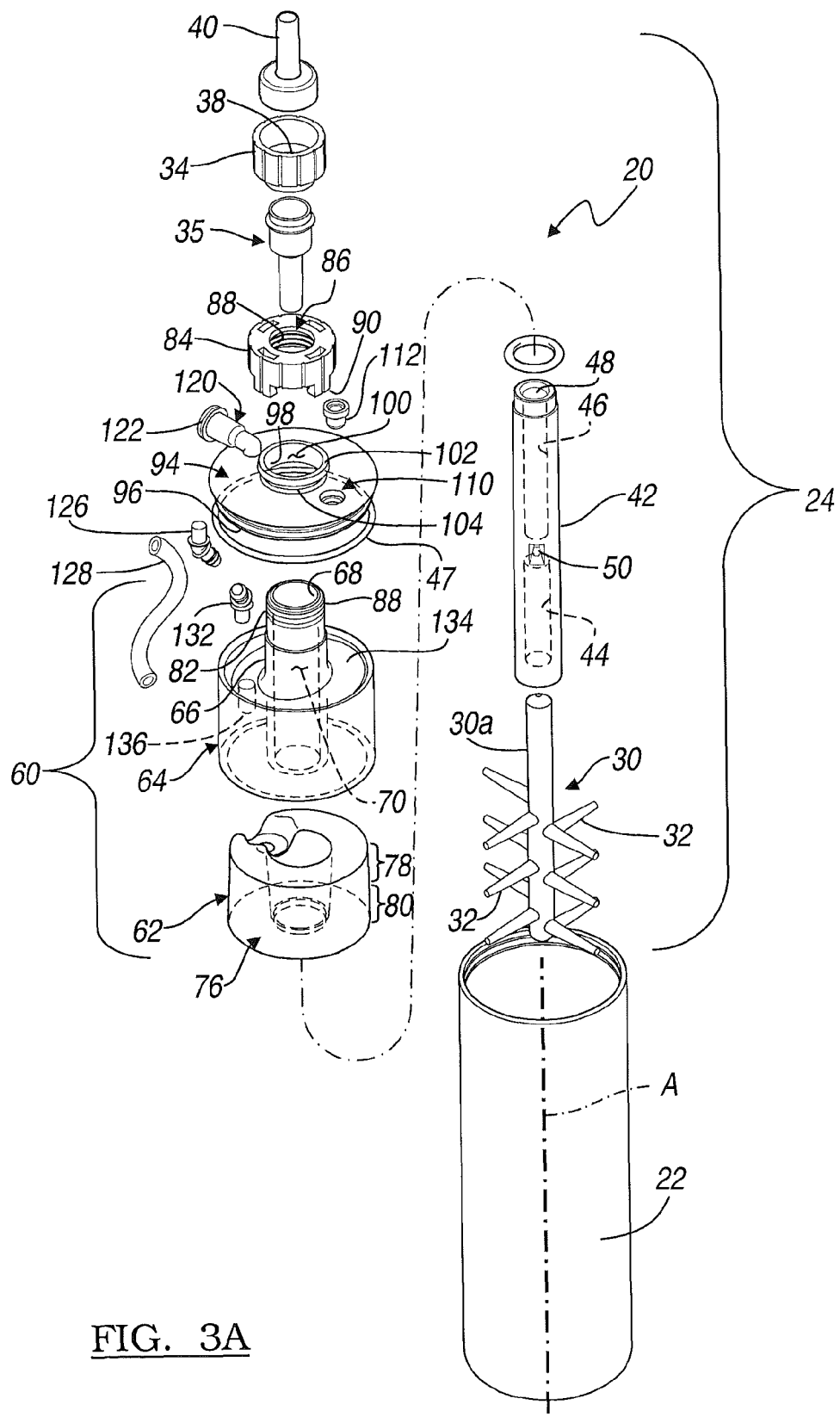
Figure 3B:
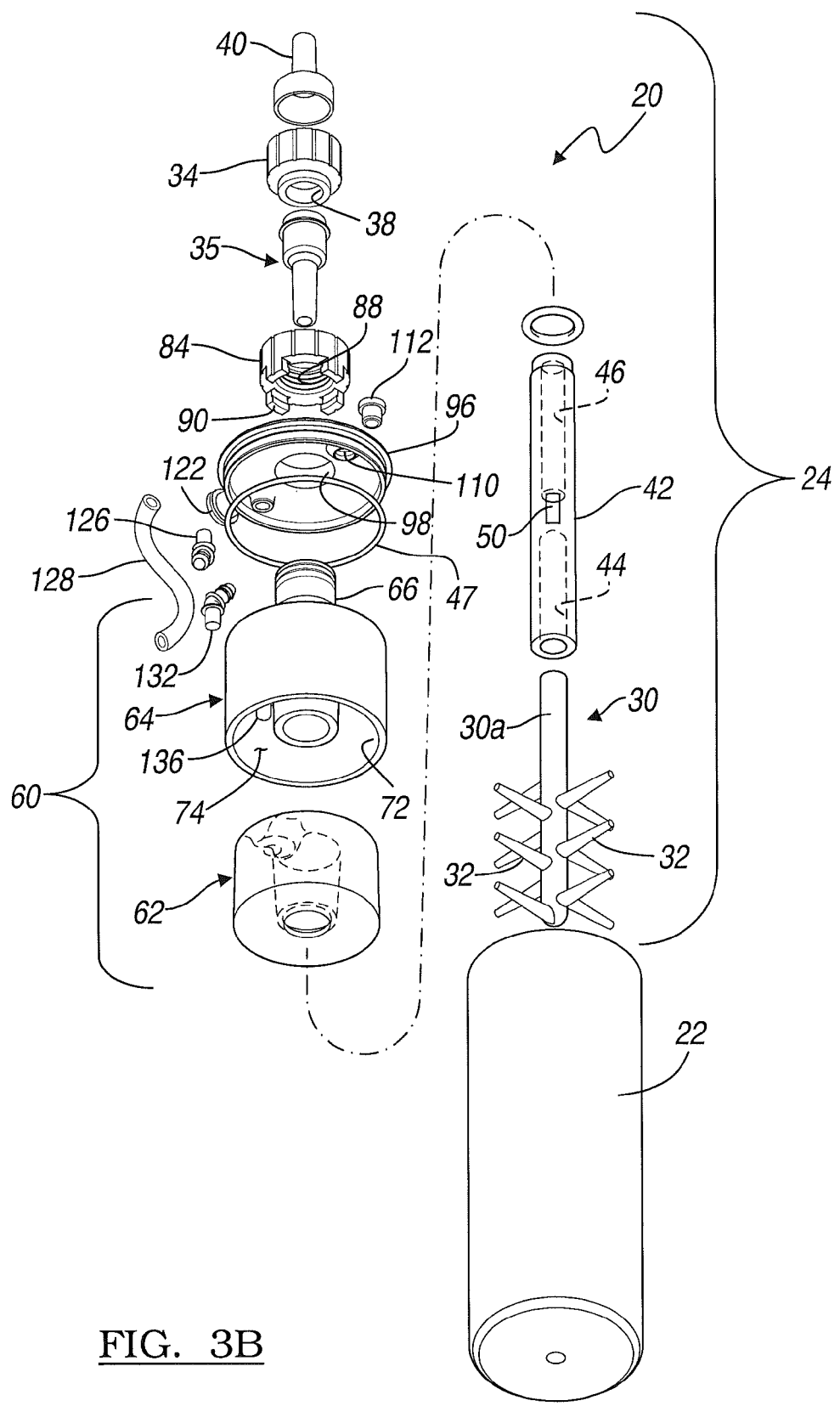
Figure 6:
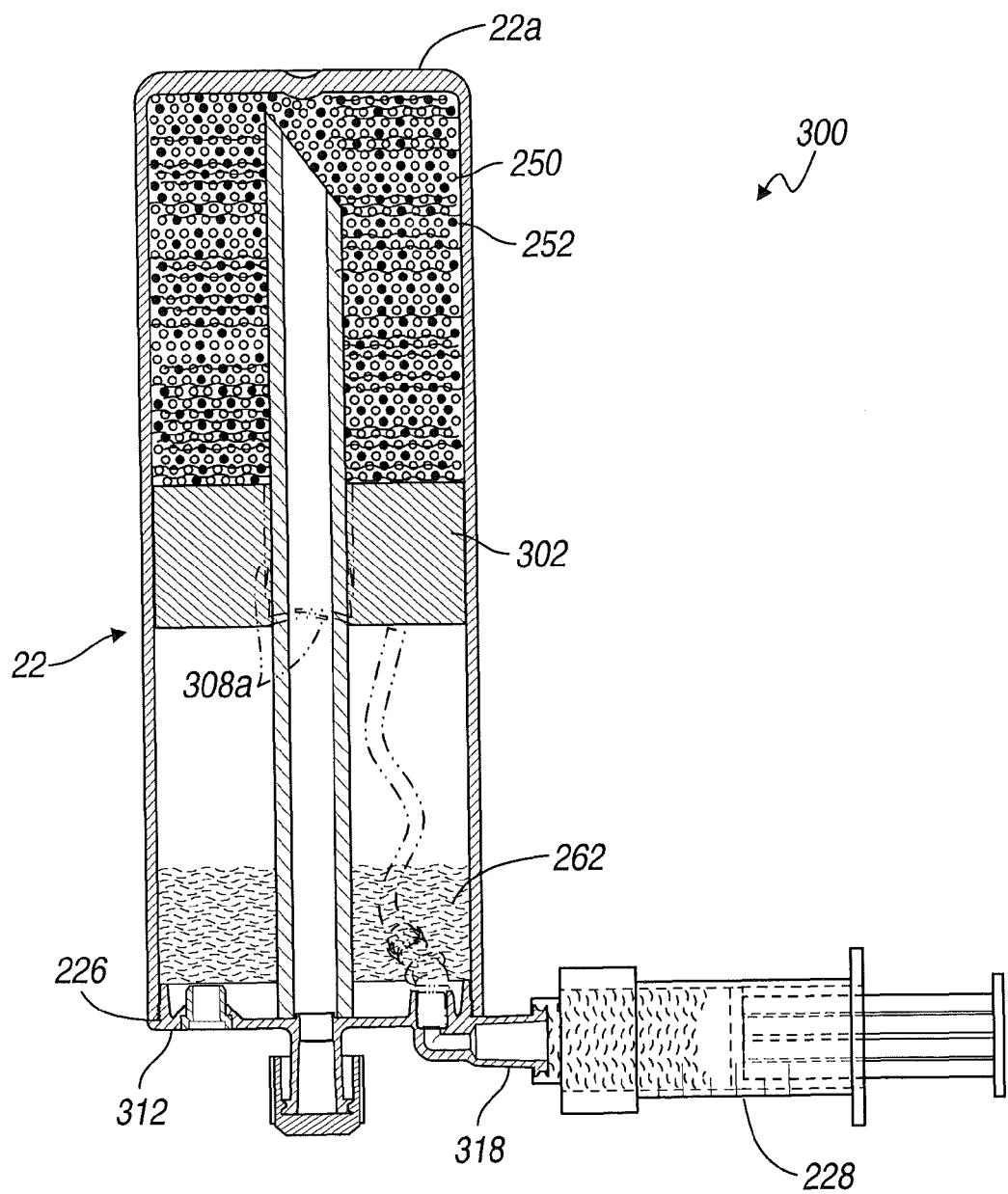
Figure 7:
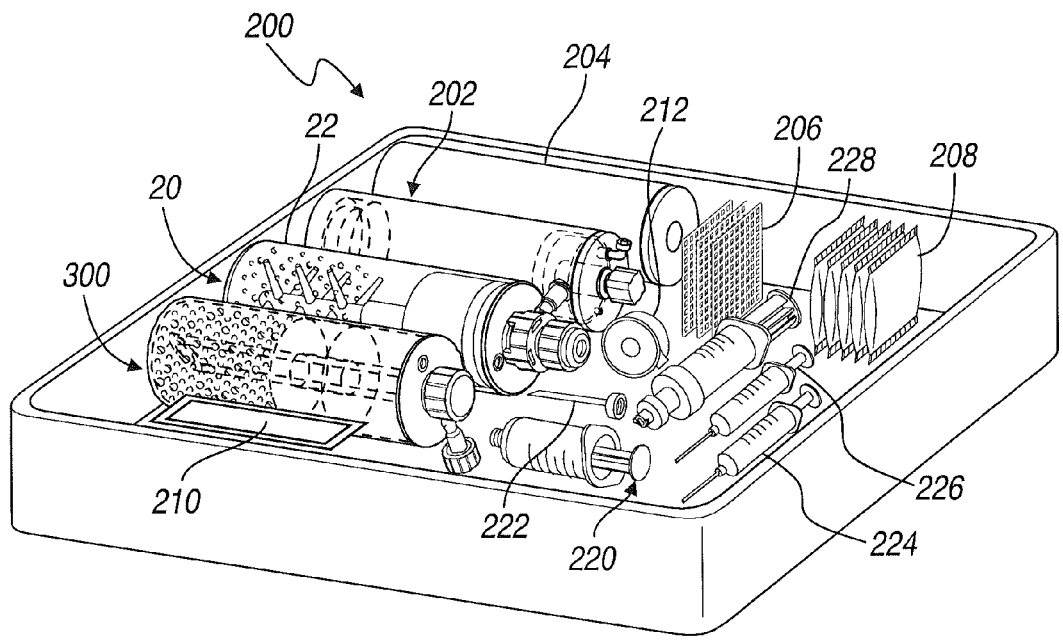
Figure 8:
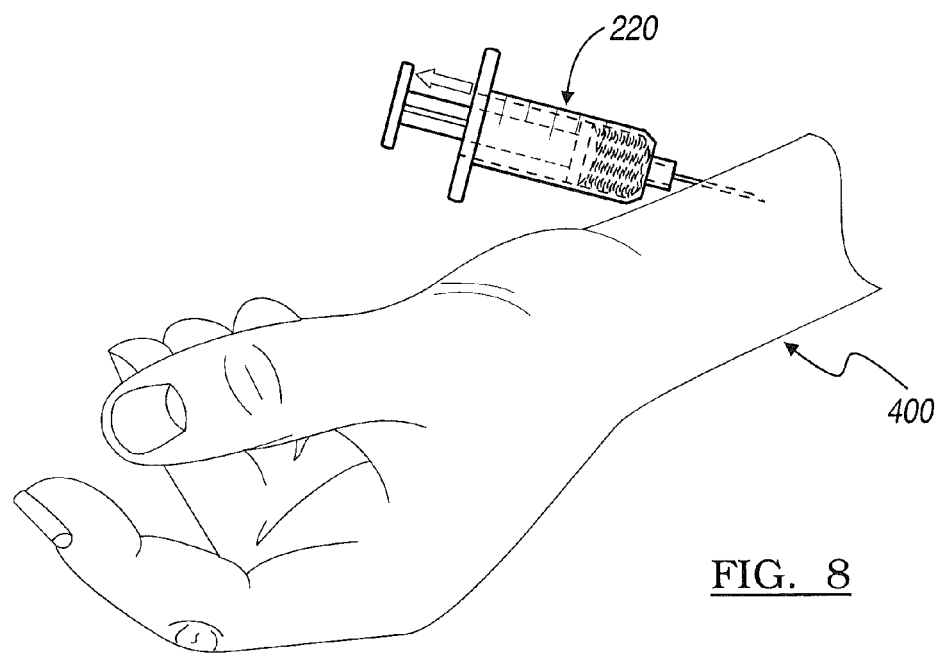
Figure 9:
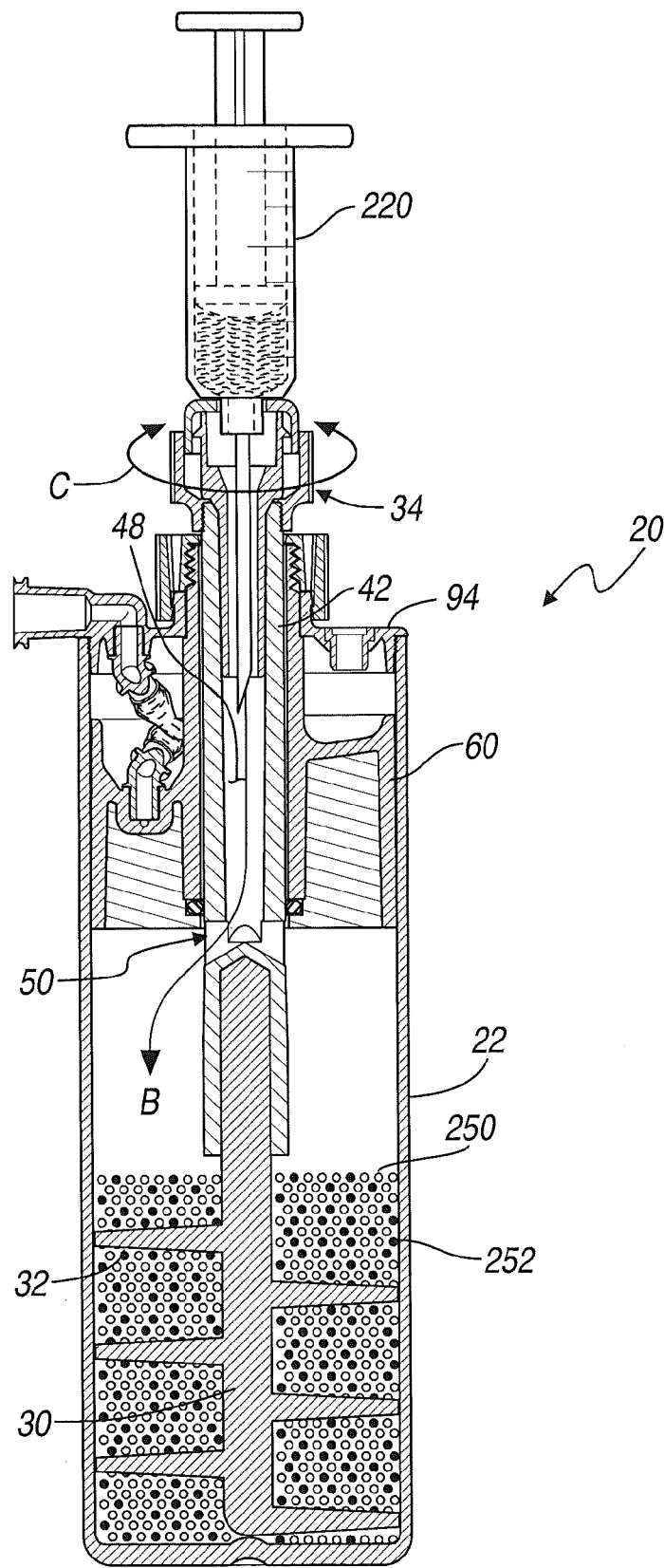
Figure 10:
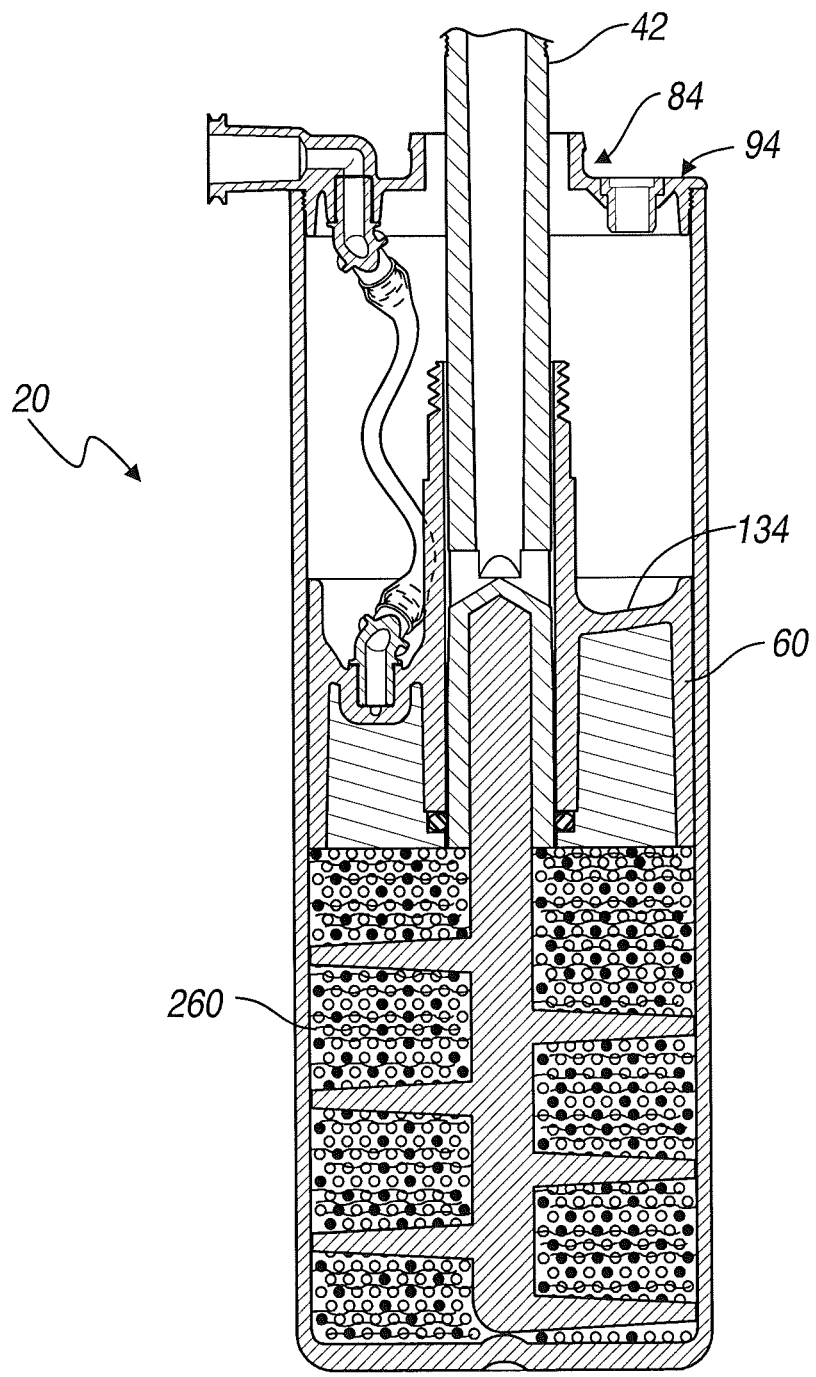
Figure 11:
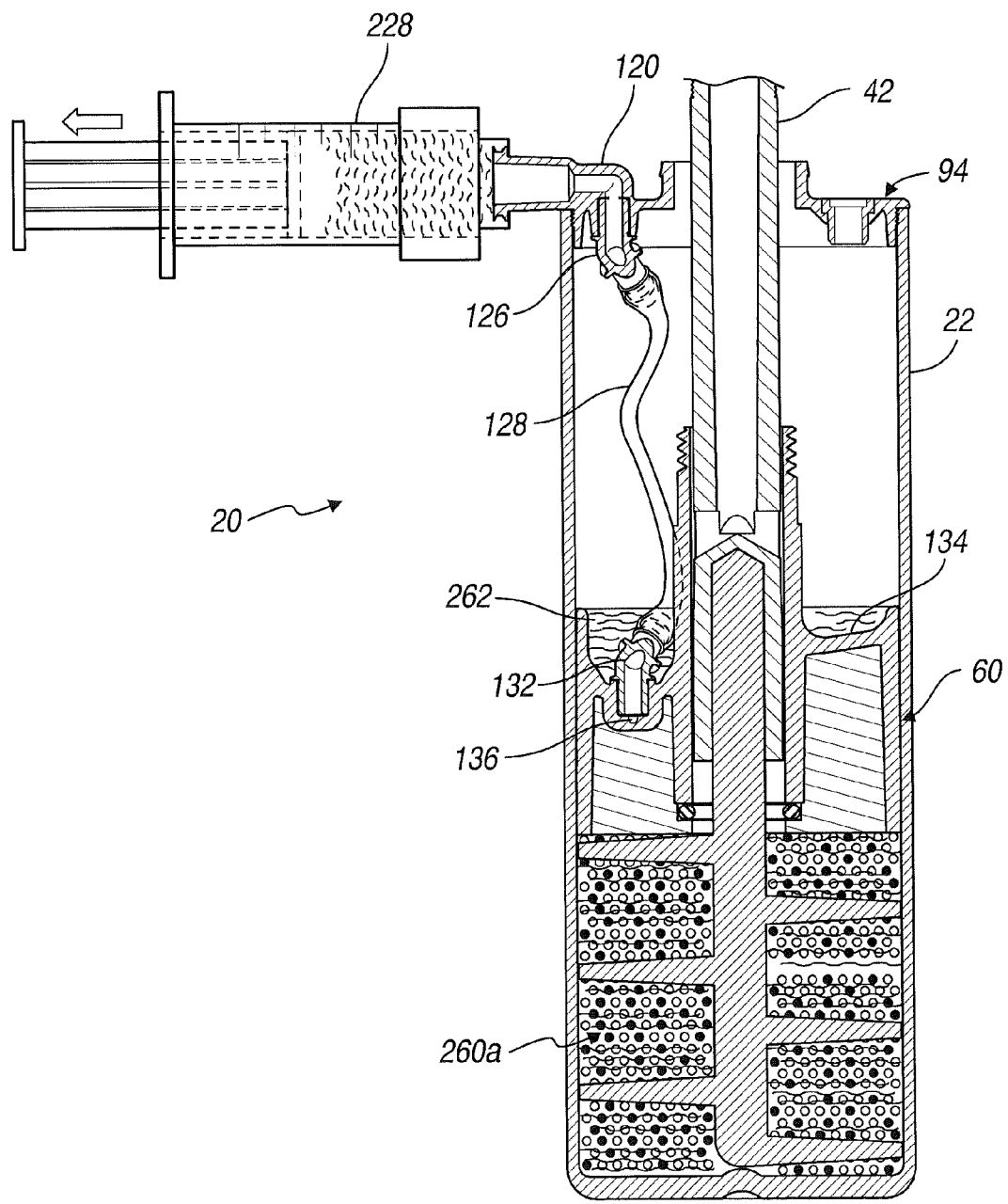

A method and apparatus is taught for providing a clotting component concentration from a source. For example, an autologous clotting component may be provided by using a source from a selected individual, such as a human being, to be implanted into the same individual. It will be understood, however, that any appropriate source may be used with the disclosed method and apparatus to produce clotting factors for use in a selected species. It will also be understood that the disclosed method and apparatus may be used to form an autologous source of thrombin for any appropriate species, such as humans or other species. Nevertheless, the method and apparatus can provide a source of clotting components, such as thrombin, for use in a selected procedure. The method and apparatus can be used to separate, concentrate, and/or collect a component of a multi-component material. The multi-component material can be any appropriate material, such as whole blood, partially separated blood, or other solu- FIG. 1 is a prospective view of a device according to various embodiments;

FIG. 2 is an assembled cross-sectional view of a device for separating a multi-component material according to various embodiments;

FIG. 3A is an exploded top perspective view of the device in FIG. 1 according to various embodiments;

FIG. 3B is an exploded bottom perspective view of the device of FIG. 1 according to various embodiments;

FIG. 4 is an exploded view of a head separating device according to various embodiments;

FIG. 5 is a cross-sectional view of an assembled device according to FIG. 4;

FIG. 6 is an environmental view of the device according to FIG. 4 in use;

FIG. 7 is a kit including various components according to various embodiments for performing a procedure;

FIG. 8 is an environmental view of withdrawing blood from a selected patient;

FIG. 9 is an illustration of introducing a multi-component sample into the device of FIG. 1;

FIG. 10 is a view of a portion of the device of FIG. 1 in an activated position;

FIG. 11 is a prospective view of a selected separated material being withdrawn from the device of FIG. 1.

DETAILED DESCRIPTION OF VARIOUS EMBODIMENTS

The following description of various embodiments is merely exemplary in nature and is in no way intended to limit the teachings, its application, or uses. Although the following teachings may be related to use for an autologous production of clotting components from a human source, it will be understood that the teachings herein are not limited thereto. It will be understood that variations within the scope of the present teachings may be used to produce a clotting component, such as thrombin, from a heterologous or a homologous source. Further, the teachings herein may be applied to producing clotting components for various species including humans, domesticated livestock, and other species.

With reference to FIGS. 1, 2, 3A and 3B, a blood separating apparatus 20 may be used to separate and concentrate a selected portion of a whole blood sample. For example, the blood separation device 20 may be used to separate and concentrate a clotting component, such as thrombin or other clotting factors. The blood separating device 20 can be used to separate any appropriate blood sample, such as from a human being, a domestic animal, or any appropriate source. It will be understood that the blood separating device 20 can also be used to separate other appropriate portions from samples that include multiple fractions or components. Nevertheless, the blood separating device 20 may be used to separate and concentrate autologous clotting components, such as thrombin.

The blood separating device 20 generally includes a container or tube 22, having an inner wall 23, and a collecting and/or activating portion 24. The tube 22 may be any appropriate tube such as the tube disclosed in U.S. patent application Ser. No. 10/445,381, filed May 23, 2003 and incorporated herein by reference. The tube 22 may be any appropriate tube, but generally includes a feature such as not binding or substantially interacting with any portion of a whole blood sample. Further, the tube 22 may be flexible, such as under a selected stress, so that a portion of the collecting portion 24 may move relative to the tube 22.

As discussed herein, the tube 22 and various portions of the collecting portion 24 may be used with a centrifuge which generally will provide an increased gravitational force generally along an axis A of the tube 22. The force along the axis A may cause the tube 22 to expand and the wall 23 of the tube 22 to increase in diameter relative to an unforced diameter of the tube 22. Nevertheless, the tube 22 may be formed of any appropriate materials such a polymer, a glass, a ceramic, or the like. Generally, the tube 22 is used to house the collecting portion 24, hold the collected whole blood sample, and hold a selected activating portion, such as selected beads discussed herein.

The activating portion 24 of the separating device 20 can include a plurality of portions that are interconnected or integrally formed to form the collecting portion 24. It will be understood although various portions of the collecting portion 24 may be described as independent or separate components herein that various portions of the collecting portion 24 may also be formed as a single piece. Therefore, discussion of separate or distinct components relative to another component of the collecting portion 24 will be understood to not limit the components to being separate or integral members but may also be formed as a single piece.

Nevertheless, the collecting portion 24 can generally include a mixing or stirring member 30 that extends a substantial length of the collecting portion 24. The mixing member 30 may be formed of a plurality of portions or may be formed as a single member that extends the length of the activating portion 24. Further, extending from an end of the activating portion 24 are a plurality of paddles or agitation members 32. The agitation members 32 may be used to agitate a selected portion of a sample positioned in the separating device 20 with various members positioned in the tube 22, as discussed herein.

The stirring member 30 may be activated in any appropriate manner such as with a knob 34 that is interconnected with the mixing member 30. The knob 34 may be formed in any appropriate manner and may include any appropriate geometry. Nevertheless, the knob 34 may be manually activated or manipulated to activate or move the mixing portion 30 and the agitation members 32 associated therewith. It will be further understood that the knob 34 may be eliminated and the mixing member 30 may simply extend to be grasped by a user. Alternatively, or in addition thereto, the knob or an alternative knob portion 34 may be interconnected with a power source or motor, such as a drill motor, to activate the mixing portion 30. Therefore, it will be understood that the mixing portion 30 may be activated in any appropriate manner such as substantially manually, with a motor, or automatically.

Associated with the mixing portion 30 is an entry or delivery port 38. The delivery port 38 may be covered with a detachable member 40 for various purposes, such as transportation and maintaining a sterile environment for a selected period of time. Nevertheless, the detachable member 40 may be removed to access the entry port 38. As discussed herein, a syringe, or other appropriate device, may be used to deliver a selected sample, such as a whole blood sample, into the tube 22 through the entry port 38.

The entry port 38 may be interconnected with a mixer shaft or delivery member 42. The mixing shaft 42 may also be interconnected with the mixer 30 in a manner that allows a force to be transferred from the mixing shaft 42 to the mixer 30. The mixer shaft 42 can define a first internal bore or circumference 44 adapted to interconnect with a proximal portion 30a of the mixer 30. The interconnection between the proximal portion 30a and the wall 44 defining the bore may be any appropriate connection and can be augmented with an adhesive material to ensure the connection between the mixer 30 and the mixer shaft 42. Alternatively, other welding techniques can be used to interconnect the mixer shaft 42 with the mixer 30.

The mixer shaft 42 can further include a proximal wall 46 defining an upper or proximal bore 48. The wall 46 can interconnect or also define a port 50 that is interconnected with the proximal bore 48. The port 50 that is interconnected with the bore 48 is further interconnected with the inlet port 38. This allows for a selected sample to be introduced from an exterior of the device 20 to an interior of the tube 22. Further, the material may be introduced, as discussed herein, when the device is substantially assembled as illustrated in FIG. 1. The removable portion 40 may be removed to access the inlet port 38 such that the sample may be provided through the proximal bore 48 and through the port 50 to inlet the material into a portion or void defined by the tube 22. As discussed herein, any appropriate material may be provided into the bore defined by the tube 22 and the port 50 is positioned such that it is substantially unobstructed by other portions of the activation device 24.

The cap 34 may define itself the needle port 38 or, and additionally and alternatively thereto, a needle port device 35 may be positioned through the cap 34. The needle port device 35 may include an extended portion or member including an inner wall 37 that is operable to be positioned within the mixer shaft 42. The needle port extension portion may engage the inner wall 46 of the mixer shaft 42 such that a needle may be positioned relative to the needle port member 35 to provide an easy access and interconnection of a needle with the device 20. As discussed herein, a needle interconnected with a source of a material may be positioned in the needle port 35 to allow the material to flow through the mixer shaft 42 and out to the port or through the port 50. It will be understood, however, that a material may be positioned in the device 20 in any appropriate manner and including the needle port device 35 interconnected with the mixer shaft 42 is merely exemplary.

The activating portion 24 further includes a piston or weight section 60. The piston section 60 may be formed as a substantially single piece or may be formed with a plurality of pieces interconnected together and positioned with the activation section 24. For example, the piston 60 may include a mass or core portion 62 that is interconnected with an upper or plunger section 64. The plunger section 64 may also define an extension or post portion 66. The post portion 66 may include an inner wall 68 that defines a bore 70. The bore 70 can be positioned relative to the mixer shaft 42 such that the mixer shaft 42 is movable relative to the inner wall 68. This can allow the piston section 60 to move relative to the mixer shaft 42 at a selected time. It will understood that the piston section 60 may move as a single member or may move as separate portions thereof.

The plunger section 64 may also define an inner wall 72 that defines an inner void 74. The inner void 74 and the inner wall 72 may be formed to substantially receive or interconnect with a portion of the core 62. Generally, the core 62 may include an exterior wall 76 that can mate or fit within the void 74. The core 62 may then be interconnected with the plunger 64 in any appropriate manner, such as with adhesives, welding methods, and/or the like.

As illustrated in FIG. 3, the core 62 may include a first or proximal circumference 78 that is smaller than a bottom or distal circumference 80. Therefore, the proximal portion defined by the proximal wall portion 78 can engage or fit within the void 74 while an additional or distal portion 80 extends therefrom. It will be understood that the core 62 may be formed in any appropriate manner, however, to interconnect with the plunger 64. Alternatively, the plunger 64 may be a substantially single piece that does not include the core 62 as a separate or interconnected component. The core 62 can be separate if it is selected to form the core of a different material than the remaining material of the plunger 64. This may be selected for various purposes, such as different characteristics, such as mass, density, or the like. Therefore, the plunger/core combination of the piston 60 may be designed of selected materials to achieve a selected mass or density for various purposes, such as those described herein.

The extension 66 of the plunger 64 includes a proximal or exterior threaded portion 80. The threaded portion 80 defines external threads 82 that are able or operable to engage a locking or engagement nut 84. The locking nut 84 includes an internal portion 86 that defines an internal thread 88. The internal thread 88 is able to engage the external thread 82 of the extension 66 of the plunger 64. The locking nut 84 also includes an engagement tang or finger 90 that engages a portion of a cap 94.

The cap 94 includes an engaging wall 96 that is able to engage the internal wall 23 of the tube 22. An O-ring 97, or other appropriate sealing member may also be provided, if selected. Defined by a center of the cap 94 is an inner wall 98. The inner wall 98 defines a bore 100 that is operable to allow or can allow the mixer shaft 42 to pass therethrough. Further, an exterior wall 102 defines a lip or underlip 104 that is able to engage or operably engages the tang's 90 of the lock nut 84. Therefore, the lock nut 84 can movably or rotatably engage the undercut area 104 such that the lock nut 84 can rotate relative to the cap 94. The rotation of the lock nut 84 relative to the cap 94 allows the internal threads 88 of the lock nuts 84 to engage the external threads 82 of the extension 66 of the plunger 64. As discussed herein, this allows the piston portion 60 to be secured relative to the cap 94 for various purposes, such as transportation of the device 20. Nevertheless, during a use, the lock nut 84 can be turned to disengage the piston section 60 from the cap 94 to allow the piston section 60 to move inside of the tube 22. Further, the lock nut 84 can be used to hold the piston section 60 relative to the cap 94 such that a material provided through the inlet port 38 is able to pass through the port 50 of the mixer shaft 42 without being obstructed by the piston portion 60.

It will be understood, however, that the piston section 60 can be held relative to the cap or in any appropriate position in the device 20 using any appropriate method or apparatus. The lock nut 84 is simply illustrated and illustrative of a mechanism to hold the piston portion 60 in a selected position relative to the remaining portions of the device 20.

The cap 94 also includes a venting port 110. The venting port 110 can include a hydrophobic filter or membrane 112 to assist in containing a material within the tube 22. Nevertheless, the venting port 110 may still allow for a gas, such as atmospheric gases, to vent from the tube 22. As discussed herein, the piston 60 can move relative to the tube 22 and the vent port 110 can assist in the easing of the movement of the piston 60 relative to the tube 22.

Further, the cap 94 includes a withdrawing or second port 120. The withdrawing port 120 can define an external thread 122 that is operable to interconnect with any appropriate connection system. Alternatively, any appropriate connection may be provided from the withdrawing port 120 such as a simple press fit, a taper fit, or the like. Extending from the cap 94 and relative to the withdrawing port 122 is a connection port or bud 126. The bud 126 extending from withdrawing port 120 can be interconnected with any appropriate member, such as a flexible tube 128. The flexible tube 128 may further interconnect with a second bud or port 132 extending from a portion of the plunger 64.

The plunger 64 defines an upper or proximal surface 134. The upper surface 134 can include any appropriate geometry such as a geometry to create a sump 136 in the upper surface 134 of the plunger 64. The sump 136 can be interconnected with the tube bud 132 such that a material that collects within the sump 136 can be drawn through the hose bud 132 and through the flexible tube 128 and out the outlet port 120. Similarly, the core 62 can include a complementary shape such that it is able to substantially fill the void 74 defined by the plunger 64 including a surface adapted to substantially complement or mate with the bottom surface of the upper surface 134. Nevertheless, it will be understood, that the plunger 134 may also include a substantially flat portion and the core 62 need not be substantially complimentary to interconnect with the plunger 64. Further, as discussed above, the plunger 64 may be substantially a single piece where the void 74 is not created but is filled with a material defining the plunger 64. According to various embodiments, the core 62 may not be selected and may not be interconnected with the plunger 64.

The device 20 exemplary illustrated in FIGS. 1-3B illustrates a device that may be exemplary used for separating a selected fraction and concentrating a fraction of a whole blood sample. For example, as briefly mentioned above, the device 20 may be used to separate and concentrate blood clotting components, such as thrombin. Although the device 20 may be used in a plurality of methods, the method illustrated below is exemplary for various embodiments and is not intended to be limiting. Further, the device 20 may be provided either as a single device or in a kit 200 including a plurality of devices and components to assist in carrying out a procedure.

Also, a member or many members may be positioned in the tube 22. The member may be a single type of member, such as an activating member or a desiccating member, or may be many types, such as both. Also the member may be various beads that can be included in the tube 22 for various purposes, such as described herein. Desiccating or drying beads 252 can be included. Activating beads 250 can, alternatively or also, be provided. Although the following description refers to beads 250, 252, it will be understood that any appropriate member or members may be used in the tube 22. The beads 250, 252 may be included in the tube 22 that assist in drying a sample positioned in the tube 22, activating a portion of the sample positioned in the tube, or other appropriate purposes. Various beads include polystyrene beads, polyacrylimide beads, glass beads or any other appropriate beads. For example, the polyacrylimide beads 252 may assist in drying the sample, such as whole blood, that is positioned within the tube 22. Polystyrene and/or glass beads 250 may activate various components of the whole blood sample to assist in the separation and concentration of the clotting component. For example, the glass beads or the polystyrene beads 250 may activate the platelets so that the thrombin that may be concentrated with the device 20. The beads may be any appropriate size such as about 0.001 millimeters to about 3 millimeters. For example, glass beads may be provided in the tube 22 that are about 2 millimeters in diameter.

With reference to FIG. 4, a device 300 according to various embodiments is illustrated. The device 300 may include a tube 22 similar to the tube used in the device 20. The tube 22 can include an internal wall 23 that defines an internal dimension such as a diameter or circumference. As discussed above, the tube 22 can be positioned in a centrifuge device and may include a selected amount of flexibility when the increased force of gravity is created due to centrifuging the tube 22.

Further, as discussed above, the tube 22 may include the activating beads 250 and the desiccating beads 252 positioned therein. The activating beads 250 and the desiccating beads 252 may be any appropriate beads, such as those discussed above.

Further, the device 300 can include a moveable piston or buoy 302. The piston or buoy 302 can include an exterior wall 304 that includes a dimension, such as a diameter or circumference, that is substantially similar or forms an interference fit with the internal wall 23 of the tube 22. The dimension of the exterior wall 304 of the piston 302 may allow the piston 302 to be held at a selected position within the tube 22 when no or a small external force is applied thereto. As discussed above, if the tube 22, including the piston 302, is positioned in a centrifuge, the force placed on the tube 22 may cause the internal dimension defined by the internal wall 23 to increase allowing the piston 302 to move within the tube, generally along an axis A. This can allow the piston 302 to move within the tube 22 at a selected time and yet be held within the tube 22 at a selected location at a selected time.

Further, the piston 302 can define an internal bore or passage 306. The internal passage 306 can define an internal wall 308 that also includes a selected dimension. The selected dimension of the passage 306 can allow a tube, such as a delivery tube 310 to pass through the passage 306. The delivery tube 310 can include an external dimension that fits snugly within the passage 306. Further, various sealing members 308a (shown in phantom) can be provided between the delivery tube 310 and the passage 306. The sealing members 308a may be any appropriate member or mechanism, such as a resiliently deformable member 308a that extends from the wall 308 and can engage the delivery tube 310 to seal a portion of the piston 302 relative to the delivery tube 310. Also, when the tube 310 is not present the sealing members 308a may seal the passage 306 to material that would otherwise pass through the passage 306. This can help a material, such as whole blood, alcohol, or other materials to not pass or move between the tube 310 and the piston 302 through the passage 306. It will be understood, however, that sealing members 308a are not required, and are merely exemplary as a mechanism for resisting passage of material between the delivery tube 310 and the piston 302 when selected.

It will be understood that the pistons 302 may be designed in any appropriate manner. For example, the piston 302 may include a top portion 309 that can be defined or designed in any appropriate shape. For example, the top 309 of the piston 302 may define a sump, similar to the sump 136 defined by the piston 60. In addition thereto, or alternatively, the top 309 of the piston 302 may define a well or recess in which selected material may collect. Nevertheless, the device 300 may also include the top 309 or the piston 302 to be substantially flat.

The delivery tube 302 can be interconnected with a cap or top member 312. The cap 312 can include a first port 314 that interconnects with the delivery tube 310. A closing or fixing cap 316 can be provided to close the port 314 at a selected time. Further, the cap 312 can define a second port 318 that can be used for various purposes, such as those discussed herein. A second closing cap 320 can be provided to interconnect with the second port 318. Further, a pressure relief valve or vent 322 can be provided and a filter or sealing member 324 can be provided to seal the port 322.

With additional reference to FIG. 5, when the device 300 is assembled, the beads 250, 252 can be positioned near a bottom or distal end 22a of the tube 22. The piston 302 can rest near the beads 250, 252 such as on a surface defined by the beads 250, 252. The delivery tube 310 that is interconnected with the cap 312, or passes substantially there through, can be used to fill the tube 22 with a selected material, such as whole blood, using a delivery device or syringe, such as the syringe 220. As discussed herein, various components, such as whole blood, can be drawn into the syringe 220 and delivered to the tube 22. The delivery tube 310 allows for the whole blood to be delivered past the piston 302 to the area including the beads 250, 252. Also, as discussed herein, various other components can be provided to the area including the whole blood and the beads 250, 252. These other materials can include ethanol, anti-coagulation components, and other appropriate components. Nevertheless, the delivery tube 310 can allow the whole blood to be passed past the piston 302 into the area of the tube 22 including the beads 250, 252 without filling an area above the piston 302 that may be a collection or removal area 330.

The force of pushing the various materials into the area including the beads 250, 252, may allow the whole blood and the other material to substantially mix with the beads 250, 252 and each other. Nevertheless, it will be understood that a user can agitate the device 300 to provide or encourage mixing of the various components. Additionally, use of the centrifuge or other device may also enhance mixing of the material.

The various materials, including the whole blood, calcium chloride, ethanol, and other appropriate or similar mixtures, can be allowed to mix and become activated with the beads 250 and dried with the desiccating beads 252, if provided, for a selected period of time. Generally, the material may be allowed to mix and react for about three minutes to about eight minutes, such as about five minutes. After the mixing/activation time, the device 300 may be positioned in a centrifuge and spun for a selected period of time, such as about 15 minutes to about 25 minutes, and such as about 20 minutes.

During the centrifugation, the piston 302 can move towards the bottom 22a of the tube 22 under the increased force produced by the centrifuge. The force allows the walls of the tube 22 to flex, allowing less dense materials to pass above or past the piston 302 into the collection area 330 as the piston moves or is forced towards the bottom 22a. One skilled in the art will understand that dense materials will move towards the bottom of the tube 22a while less dense materials, including various clotting factors such as thrombin, may move into the collection area 330 because they are less dense than other components of the whole blood. Nevertheless, after the end of the centrifugation, the piston 302 can be held at a selected location within the tube 22 due to the interaction of the piston 302 with the internal wall 23 of the tube 22.

As illustrated in FIG. 6, due to the positioning of the piston 302, the beads 250, 252 and other components, such as other components of the whole blood, are held near the bottom 22a of the tube 22. The selected clotting factors or components 262 can be positioned near a top 22b or near the cap 312 by inverting the tube 22 so that the force of gravity moves the clotting components 262 near the cap 312 as opposed to the bottom 22a of the tube 22. The clotting components 262 can then be aspirated or removed through the second port 318 by a selected device, such as a collection syringe 228.

It will be understood that the delivery tube 310 can remain in the tube 20 during the entire centrifuge step and need not be removed. The delivery tube can be used to deliver material to an area past the piston 302 near the distal end 22a of the tube 20. In addition, the delivery tube 210, according to various embodiments, can be used to withdraw material from near the distal end 22a of the tube 20 as well. According to various embodiments the delivery tube 310 may also be removed from the tube 20 prior to or after centrifugation of the material in the tube 20. The sealing portion 308a on the piston may seal the passage 306 if the delivery tube is removed from the tube 20 in such an instance.

Further, the device 300 may include a collection tube 319 that interconnects with the second port 318, although the collection tube 319 is optional. The collection tube 319 can be used to withdraw material from the collection area 330 similar to the tube 128 described in relation to the device 20. It will be understood, however, that the collection tube 319 need not be provided and the device 300 may simply be inverted, as illustrated in FIG. 6, to withdraw the selected clotting components or other selected component from the separation device. Generally, if the collection tube 319 is provided the device will not be inverted to withdraw the selected material. Also, it will be understood that the collection tube 319 may be provided to reach an area near the distal end of the tube 22a and past the piston 302 to withdraw a selected material that may be collected near the underside of the piston 302 and near the distal end of the tube 22a.

Therefore, the device 300 can allow for a simple and efficient collection of various components, such as clotting components, from a selected source. For example, during a procedure the clotting components 262 can be used in an autologous fashion such that the whole blood sample introduced into device 300 can be centrifuged to allow for the formation of autologous clotting components that can be withdrawn into the extraction syringe 228 and reintroduced to the patient for a selected purpose.

It will be understood that the clotting components 262 can be created according to various embodiments, such as those discussed herein and according to the method described hereinafter. Therefore, it will be understood that the device 300 is merely exemplary of various embodiments and the described method of using the device 300 is merely exemplary and any appropriate method may be used. Further, the composition of the beads 250, 252 may be any appropriate composition. Also, the components mixed with the whole blood and the beads 250, 252 may be any appropriate compositions other than calcium chloride and ethanol.

With reference to FIG. 7, the kit 200 may include the selected devices, such as the devices 20 and/or 300 for use in a selected procedure. Either or only one of the devices 20 or 300 may be provided in the kit 200. If both of the devices 20, 300 are provided in the kit 200, a user, such as a physician, can select to use either or both of the devices for appropriate reasons. Therefore, it will be understood that reference to the blood separation device 20 will also be a reference to blood separation device 300 for discussion and use of the kit 200.

The kit 200 may also include a blood separating system 202 such as that described in U.S. patent application Ser. No. 10/445,381, filed May 23, 2003 and incorporated herein by reference. The blood separation device 202 may be used in tandem with the blood separation device 20 or may be used separately therefrom. Regardless, the blood separation device 20 and the blood separation device 202 may be a part of the kit 200 to assist in performing a procedure. Also, a blank or empty container 204 which may be substantially similar to the tube 22 may be included in the kit 200. The blank container 204 may be used to balance a centrifuge when using the blood separation device 20. This may be selected for various centrifugation devices or appropriate procedures for balancing the centrifuge.

In the kit 200, the tube 22 of the device 20 may also contain the beads, such as the activating beads 250, and the desiccating beads 252. Alternatively, or in addition thereto, the beads 250, 252 may be provided separately in the kit 200 to be added to the tube 22 at a selected time. Therefore, it will be understood that the beads 250, 252 illustrated within the tube 22 may not necessarily be provided in the tube 22 but may be provided separately and/or individually in the kit 200.

Further, the kit 200 may include various instruments or portions that assist in performing a procedure with the device 20. For example, gauze pads or swatches 206 may be provided to assist in the procedure. Also preparation pads such as alcohol prep pads 208 may be provided. Also various labeling portions such as labels to label with a patient name or identification 210 may be provided. Also an appropriate adhesive 212 may be provided for assisting in the procedure such as adhering various components of the kit 200 together for a selected procedure.

The kit 200 may also include a sample collecting syringe 220. The sampling selecting syringe 220 may be any appropriate syringe and may be interconnectable with a selected needle 222. The sample collecting syringe 220 may be used in a generally known manner to collect a selected sample, such as a whole blood sample. For example, the syringe 220 may be interconnected with an intravenous (IV) port, create a blood vessel access using the needle 222, or any other appropriate method to obtain a sample. Generally, the syringe 220 can be used to collect a sample of approximately 30 milliliters. Although it will be understood that the sample collected may be any appropriate sample size for use with the device 20 or the device 202.

The kit 200 may also include other appropriate components such as a syringe 224 that can contain a selected amount of ethanol (EtOH) to be mixed with the various portions of the sample. Further, the kit 200 may include a syringe 226 that may include a selected volume of calcium chloride (CaCl$_2$) that may also be mixed with a selected portion of the sample. Also the kit 200 may include an extraction or component collection syringe 228 that may be used to withdraw the separated component, such as the concentrated clotting components from the device 20. As discussed herein, the various components, such as the ethanol and the calcium chloride, may be mixed with the whole blood sample to assist in the concentration and extraction of the selected component. Therefore, these compounds or solutions may be provided in the kit 200 for performing a procedure therewith.

As discussed above, the kit 200 may be used with an appropriate procedure for various purposes. For example, the kit 200, including the device 20, may be used to separate and concentrate clotting components from a whole blood sample. Therefore, the kit 200 may be provided as a substantially complete kit to assist a user, such as a surgeon or a nurse, in obtaining a clotting factor concentrated sample from a whole blood sample. For example, the kit 200 may be used during a surgical procedure to obtain an autologous clotting factor sample from a patient. An exemplary method is illustrated in FIGS. 5-8 for preparing such a sample. It will be understood that the method taught herein is merely exemplary and illustrative of a method of using the kit 200 or any appropriate kit according to various embodiments or the device 20. That is, it is understood that the kit 200 is merely exemplary and the device 20 may be provided alone according to various embodiments for performing or assisting in a procedure.

With initial reference to FIG. 5, a sample may be collected in the sample syringe 220 from a patient 300. For example, the sample collected in the sample syringe 220 may be collected from a selected blood vessel found in an arm of the patient 300. Various techniques for obtaining the sample are generally known in the art and a particular or specific method is not required. Once the sample is collected, it may be provided to the blood separating device 20.

With reference to FIG. 6, once the blood sample is collected in the sample syringe 220, it may be inputted into the device 20 through the inlet port 38. The blood collected in the sample syringe 220 may be expressed through the mixing shaft 42 and the bore 48 defined therein. The blood may generally follow a path along arrow B through the port 50 and into the void defined by the tube 22. As discussed above, also included in the void defined by the tube 22 may be a plurality of the beads 250, 252. The beads 250, 252 may include activating, such as glass or polystyrene, beads 250 and desiccating, such as polyacrymide, beads 252. The beads 250, 252 may be provided in the tube 22 during shipment or manufacturing of the device 20 or may be added by a user at an appropriate time. It will be understood any appropriate number and/or density of the beads 250, 252 may be provided. The number of the beads 250, 252 in the Figs. is merely exemplary and for clarity of the present disclosure.

Once the sample, such as the whole blood sample is added into the tube 22, the stirrer 30 including activation members 32 can be used to agitate the beads 250, 252 to substantially mix the whole blood sample with the beads 250, 252. The stirrer 30 may be activated with the stirrer knob 34 that is interconnected with the stirrer 30 via the stirring tube 42.

The stirrer 30 can be interconnected with the stirring rod 42 at any appropriate time such that the piston 60 is held above or nearer the cap 94 than the paddles 32. Nevertheless, this interconnection can be made during manufacturing or just prior to use of the device 20. Regardless of when the stirrer 30 is interconnected with the stirring rod 42, the stirring assembly of the stirrer 30 and the stirring rod 42 can be operated in any appropriate manner to agitate the beads 250, 252 to substantially mix them with the sample positioned in the tube 22. Generally, the activation knob 34 can be rotated in the direction of arrow C either continually in one direction or back and forth to substantially thoroughly mix the sample with the beads 250, 252.

Generally, the beads 250, 252 are provided for both drying the sample, such as the whole blood, and activating the platelets therein. It will be understood that the beads 250, 252 may be selected of any appropriate material to achieve these or various selected tasks. For example, the bead 250, as discussed above, can be either glass or polystyrene. Either the glass beads or the polystyrene beads can activate the platelets in the whole blood sample to release thrombin or other clotting components. Therefore, the activating beads 250, that may be the polystyrene or the glass beads, can assist in separating a selected blood component. The polyacrylamide beads 252 may be any appropriate material that may assist in drying or removing water from the whole blood sample. Removing water from the whole blood sample can assist in concentrating any fraction drawn or separated from the whole blood. Nevertheless, the drying beads 252, that may be polyacrylamide, can be any appropriate material.

Regardless of the materials chosen, it may be selected to include an amount of polyacrylamide beads so that about 0.10 grams to about 0.20 grams of the polyacrylamide resin in the beads to about 1 millimeter of whole blood is achieved. In addition, if polystyrene is selected for the beads 250, it may be selected to achieve about 0.0170 grams to about 0.0230 grams of the polystyrene resin to about 1 milliliter of the whole blood sample. It will be understood that any appropriate concentrations of the selected resins may be achieved to the whole blood sample and these are merely illustrative.

Once the whole blood sample is provided to the tube 22 from the syringe 220, a volume of calcium chloride may be provided from the syringe 226. The amount of calcium chloride provided may be any appropriate amount and may be dependent upon various factors. Nevertheless, about 0.010 milliliters to about 0.025 milliliters of one molar calcium chloride may be added per milliliter of whole blood sample provided to the tube 22. The calcium chloride may be mixed with the whole blood sample with the beads 250, 252 using the stirring assembly. Generally, mixing may occur for about 10 to about 60 seconds or more with the calcium chloride, the whole blood, and the beads 250, 252. Once the mixing is substantially thorough, other components may be added, such as ethanol.

Further, as discussed above, the kit 200 may include a syringe 224 that includes a selected volume of ethanol. The ethanol included in the syringe 224 may be substantially 100 percent pure ethanol, at least as pure as achievable by current methods. The ethanol is added to the mixture of the beads 250, 252 and the whole blood including the calcium chloride solution previously added approximately 10 seconds to about twenty minutes after mixing has begun.

The amount of ethanol added can be any appropriate amount, such as the amounts taught in U.S. Pat. No. 6,472,162 to Phillip Coelho assigned to Thermal Genesis Corp., incorporated herein by reference. It may be selected to achieve a concentration of ethanol that is about 4 percent to about 7 percent, for example, about 4.5 percent to about 6.5 percent of the whole blood sample. For example, it may be selected to provide about 0.045 to about 0.065 milliliters of the 100 percent ethanol to about each 1 milliliter of the whole blood sample. The ethanol assists in achieving a selected clot formation over a period of minutes and may assist in the extraction of the thrombin material, or other appropriate clot components, from the whole blood sample.

Although the ethanol may be added at any appropriate time, such as between about 10 seconds and about 15 minutes after mixing the calcium chloride, the whole blood sample, and the beads 250, 252, the ethanol may be added for assisting in appropriate clot formation times.

With reference to FIG. 7, once the appropriate mixture has been achieved, a fluid bed 260 of the mixture of the whole blood, the ethanol, the calcium chloride, and the beads 250, 252 is formed. Once the mixture 260 is formed, the locking nut 84 can be used to disengage the piston assembly 60 from the cap 94. Once the piston 60 is disengaged from the cap 94, it is free to move through the tube 22 and engage a portion or rest upon the mixture 260. It will be understood that the piston assembly 60 may not immediately drop to the top of the mixture 260 because of various forces, such as friction, but it will understood that the piston 60 will be able to move relative to the tube 22.

The piston 60, such as discussed above, may include any appropriate mass or density. For example, the piston may be about 20 to about 30 grams. The mass of the piston 60 is operable to engage the mixture 260 for various purposes, such as assisting and separating the clotting components, including thrombin, from the mixture 260.

The mixing of the whole blood with the beads 250, 252 assists in releasing the thrombin and other clotting components from the whole blood sample. Therefore, the thrombin and other clotting components are separated from the whole blood sample and may be further separated with various actions, such as centrifugation.

Therefore, once the piston 60 has been released from the cap 94, the blood separation device 20 may be placed in a centrifuge. The centrifuge may then be operated according to various specifications, such as about 3,000 rpm to about 4,000 rpm for a selected period of time. For example, a centrifuge may be operated for about 5 minutes at about 3,200 rpms with the piston 60 freed from the cap 94 in the device 20. As discussed above, the blank tube 204 provided in the kit 200 or the blood separation device 202 provided in the kit 200 may be used to balance the centrifuge.

During the centrifugation, the piston 60 is pressed against the mixture 260. The pressure of the piston 60 against the mixture 260 assists in moving the thrombin and other clotting component rich material to a proximal end of the device 20 or to the collection area 134 defined by the plunger 64. Further, as the device 20 is centrifuged, the walls of the tube 22 may flex to assist in reducing friction and other forces on the piston 60 such that it is operable to engage the mixture 260 in a selected manner.

With reference to FIG. 8, once centrifugation is complete, the piston 60 may be moved a distance relative to a distal end of the tube 22 thereby separating a clotting component rich solution 262 from the mixture 260 thus leaving a clotting component poor mixture 260a in the distal or bottom end of the tube 22. The collection area 134 of the plunger 64 provides a well for collecting and maintaining the solution 262 separate from any other portion of the device 20 and particularly the clotting component poor mixture 260a.

Once the clotting component rich fluid 262 is collected in the collection area 134, the component collecting syringe 228 can be interconnected with the outlet port 120 extending from the cap 94. As discussed above, the outlet port 120 is interconnected with the flexible conduit 128 to the sump 136 defined by the plunger 64. The tube bud 132 allows for material to be drawn from the sump 136 through the flexible conduit to 128 into the collection syringe 228. In this way, the clotting component rich fluid 262 can be drawn into the collection syringe 228 and used for any appropriate purpose.

For example, the thrombin and other clotting components collected in the clotting component rich solution 262 can be combined with other appropriate components to form a selected material, such as a fibrin or other biological glue. Regardless, the device 20 assists in providing the separation and concentration of various autologous clotting components such as thrombin, from a whole blood sample. The procedure can generally be performed in an appropriate amount of time, such as during a procedure so that a whole blood sample can be drawn from a patient and the clotting component rich solution 262 can be used in the same procedure. As discussed above, it will be understood that various other components and variations may be made in the device 20 to achieve substantially similar results and such variations are intended to be within the scope of the present teachings.

It will be understood that the blood separation devices 20, 300 can be used for any appropriate purposes, such as separating a selected component from a whole blood sample or an otherwise multi-component material. Although a selected method has been described for using both the device 20 and the device 300, it will be understood that any appropriate method may be used with either of the devices. Further, both of the devices 20, 300 can be used in a selected procedure either together or alternatively to obtain a selected fraction or component from a selected multi-component material, such as a whole blood sample. Therefore, it will be understood that the use of the device 20 does not restrict or eliminate the use of the device 300 or vice versa. Rather, either of the devices 20, 300 may be used for selected purposes as described above.

What is claimed is:

1. A method of separating a clotting component from a whole blood sample in a container having a mixing assembly and a member, comprising:

collecting a whole blood sample;

introducing the whole blood sample into a single chamber of the container;

manipulating the mixing assembly to mix the whole blood sample with the member to at least one of activate a portion of the whole blood sample or to withdraw a selected volume of water from the whole blood sample, wherein the mixing assembly includes a central member with radially extending agitation members;

moving a piston within the single chamber of the container to compress the mixture of the whole blood sample and the member towards a first end of the container, wherein the compression with the piston at least assists in moving a selected component of the whole blood sample between a proximal surface of the piston and a second end of the container away from the first end; and withdrawing a volume of a fluid including concentrated clotting components from the single chamber of the container after mixing the whole blood sample with the member.

2. The method of claim 1, wherein collecting a whole blood sample includes drawing from a patient a selected volume of whole blood.

3. The method of claim 2, wherein withdrawing a volume of a fluid including concentrated clotting components includes withdrawing an autologous concentrated clotting component.

4. The method of claim 3, further comprising:
applying the concentrated clotting components to the patient from which the whole blood sample was collected.

5. The method of claim 1, further comprising:
passing the collected whole blood sample through a first port defined in a portion of the container.

6. The method of claim 5, further comprising:
moving the collected whole blood sample past a piston disposed in the single chamber of the container to a void defined by the single chamber of the container to be mixed.

7. The method of claim 1, further comprising:
positioning the member into the container.

8. The method of claim 1, further comprising:
positioning at least one of a desiccating member and an activating member as the member in the container.

9. The method of claim 8, wherein the member includes a bead positioned in the container.

10. The method of claim 1, further comprising:
assembling the mixing assembly relative to the piston and positioning both the mixing assembly and the piston in the container such that the mixing assembly is operable to mix the whole blood sample with the member by rotating the central member to move the agitation members.

11. The method of claim 1, further comprising:
centrifuging the container including the mixed whole blood sample with the member.

12. The method of claim 10, further comprising:
collecting a volume of material including a concentration of clotting components higher than a concentration of the clotting components in the whole blood sample on a first side of the piston and higher in the container and moving the piston lower in the container due to centrifuging the container;
wherein introducing the whole blood sample into the container is introducing the whole blood sample to a second side of the piston opposite the first side.

13. The method of claim 1, further comprising at least one of:
admixing ethanol to the mixed whole blood sample; or
adding calcium chloride to the container and mixing the whole blood sample with the calcium chloride and the member.

14. The method of claim 1, further comprising:
forming a clot of the concentrated clotting components with a selected material for positioning relative to a patient from which the whole blood sample was collected and from which the concentrated clotting components were formed.

15. The method of claim 9, wherein mixing the whole blood sample with the desiccating member and the activating member includes manually manipulating the mixing assembly from a position exterior to the container.

16. The method of claim 1, further comprising:
centrifuging the whole blood sample and the piston within the container to cause the piston to move within the container;
wherein the piston moves towards the first end of the container away from the second end of the container.

17. The method of claim 1, wherein withdrawing the volume of fluid, includes:
moving the volume of fluid through a flexible member interconnecting a cap and the piston movable within the container, wherein the flexible member is positioned near a sump defined by the piston.

18. A method of separating a clotting component from a whole blood sample in a container having a mixing assembly and a member, comprising:
collecting a whole blood sample;
introducing the whole blood sample into a volume of the container;
manipulating the mixing assembly to mix the whole blood sample with the member within the volume to at least one of activate a portion of the whole blood sample or to withdraw a selected volume of water from the whole blood sample, wherein the mixing assembly includes a plurality of radially extending agitation members;
centrifuging the container to move a piston within the volume to at least assist in separation of a fluid including concentrated clotting components; and
withdrawing a volume of the fluid including concentrated clotting components from the volume of the container after mixing the whole blood sample with the member.

19. The method of claim 18, wherein manipulating the mixing assembly to mix the whole blood sample with the member includes manually manipulating the mixing assembly from a position exterior to the container.

20. The method of claim 19, wherein manipulating the mixing assembly to mix the whole blood sample with the member occurs prior to centrifuging the container.

21. The method of claim 18, wherein introducing the whole blood sample into the volume of the container includes introducing at least a portion of the whole blood sample through at least a bore formed through the mixing assembly into the container.

22. The method of claim 18, further comprising:
disengaging the piston from a portion of the container such that the piston is operable to move within the container and a portion of the fluid moves past the piston during the centrifuging the container to move the piston.

23. The method of claim 18, wherein the member includes at least one of a desiccating bead or an activating bead.

24. The method of claim 18, further comprising:
providing a passage though the piston to allow the volume of fluid to pass the piston and move towards a top wall of the container; and providing a withdrawing port formed near the top wall to allow access the volume of fluid that has moved past the piston.

25. The method of claim 18, wherein the plurality of agitation members extend radially from a main member are spaced longitudinally and circumferentially around the main member.

26. The method of claim 22, wherein engaging the piston from the portion of the container includes:
moving a locking member having an internal thread to disengage an exterior threaded portion of the piston.

27. A method of separating a clotting component from a whole blood sample in a container having a mixing assembly and a member, comprising:
collecting a whole blood sample;
introducing the whole blood sample into a single chamber defined by a wall of the container through a bore defined by a mixing assembly, wherein the single chamber of the container further contains the mixing assembly and the member, wherein the mixing assembly includes a plurality of radially extending agitation members;
manipulating the mixing assembly to mix the whole blood sample with the member within the single chamber to at least one of activate a portion of the whole blood sample or to absorb a selected volume of water from the whole blood sample; and
withdrawing a volume of a fluid including concentrated clotting components from the single chamber of the container after mixing the whole blood sample with the member.

28. The method of claim 27, further comprising:
centrifuging the container including the mixed whole blood with the member to assist in concentrating clotting components, wherein the centrifugation causes a piston to move within the single chamber to assist in separating the clotting component from other components of the whole blood sample.

29. The method of claim 28, further comprising:
disengaging the piston from a portion of the container such that the piston is operable to move within the container during centrifuging the container and allow at least a portion of the whole blood to move past the piston.

30. The method of claim 27, wherein the mixing assembly includes a shaft extending through at least a portion of the wall of the container and a projection extending transverse to the shaft and into the singe chamber.

* * * * *